(12) United States Patent
Saba

(10) Patent No.: US 12,040,101 B2
(45) Date of Patent: Jul. 16, 2024

(54) HIGH-PASS RADIATION SHIELD AND METHOD OF RADIATION PROTECTION

(71) Applicant: Valiallah Saba, Tehran (IR)

(72) Inventor: Valiallah Saba, Tehran (IR)

(73) Assignee: Salamatgostar Partomoj Company, Tehran (IR)

( * ) Notice: Subject to any disclaimer, the term of this patent is extended or adjusted under 35 U.S.C. 154(b) by 403 days.

(21) Appl. No.: 17/561,314

(22) Filed: Dec. 23, 2021

(65) Prior Publication Data

US 2022/0165442 A1    May 26, 2022

Related U.S. Application Data

(63) Continuation-in-part of application No. PCT/IB2019/057770, filed on Sep. 16, 2019.

(51) Int. Cl.
*G21F 3/00* (2006.01)
*A61B 6/10* (2006.01)

(52) U.S. Cl.
CPC .............. *G21F 3/00* (2013.01); *A61B 6/107* (2013.01)

(58) Field of Classification Search
CPC ................................ G21F 3/00; A61B 6/107
See application file for complete search history.

(56) References Cited

U.S. PATENT DOCUMENTS

| | | | | |
|---|---|---|---|---|
| 3,114,839 A | * | 12/1963 | Peters ................ | G21F 1/125 250/515.1 |
| 4,670,658 A | * | 6/1987 | Meyers ............... | G21F 1/12 442/131 |
| 4,795,654 A | * | 1/1989 | Teleki ................ | G21F 1/125 428/656 |
| 6,320,938 B1 | * | 11/2001 | Hopper .............. | G21K 1/10 378/18 |
| 6,429,432 B1 | * | 8/2002 | McNaught .......... | G01T 1/1648 250/363.02 |
| 6,605,818 B1 | * | 8/2003 | Cornog .............. | H05K 9/0024 250/517.1 |
| 7,041,995 B2 | * | 5/2006 | Eder .................. | G21F 1/08 250/516.1 |
| 7,211,814 B2 | * | 5/2007 | Cadwalader ........ | G21F 3/02 378/185 |

(Continued)

OTHER PUBLICATIONS

International Search Report of Dec. 9, 2019 in PCT/IB2019/057770.

*Primary Examiner* — Sean M Luck
(74) *Attorney, Agent, or Firm* — Bajwa IP Law Firm; Haris Zaheer Bajwa

(57) ABSTRACT

A high-pass radiation shield for using during radiological examinations is provided. The shield comprises: a first sublayer having a first radiation attenuation material of atomic number from 21 to 30; and a second sublayer having a second radiation attenuation material of atomic number 56 or greater. The weight of the second radiation attenuation material is not greater than the weight of the first radiation attenuation material. The shield is configured for placement on a patient's body over the entire or a portion of the field of view (FOV) for protection of the organs, especially radiosensitive organs against radiation dangers emitted by an X-ray tube without degrading image quality.

20 Claims, 10 Drawing Sheets

(56) References Cited

U.S. PATENT DOCUMENTS

| | | | | |
|---|---|---|---|---|
| 8,354,658 B1* | 1/2013 | Smith | | G21F 1/125 |
| | | | | 250/516.1 |
| 8,487,287 B2* | 7/2013 | Cadwalader | | G21F 3/02 |
| | | | | 250/519.1 |
| 8,754,389 B2* | 6/2014 | Khandkar | | G21F 3/00 |
| | | | | 250/516.1 |
| 9,754,690 B2* | 9/2017 | Rebar | | G21F 1/106 |
| 2003/0010939 A1* | 1/2003 | DeMeo | | G21F 3/02 |
| | | | | 250/516.1 |
| 2004/0004196 A1* | 1/2004 | DeMeo | | B32B 27/18 |
| | | | | 250/516.1 |
| 2005/0211930 A1* | 9/2005 | DeMeo | | G21F 3/02 |
| | | | | 250/516.1 |
| 2006/0049384 A1* | 3/2006 | Eder | | G21F 1/12 |
| | | | | 252/478 |
| 2006/0217477 A1* | 9/2006 | Ballsieper | | G21F 1/106 |
| | | | | 524/588 |
| 2006/0224034 A1* | 10/2006 | Reever | | G21F 3/00 |
| | | | | 600/3 |
| 2007/0075277 A1* | 4/2007 | Smith | | G21F 3/02 |
| | | | | 250/515.1 |
| 2008/0164425 A1* | 7/2008 | Cadwalader | | A61B 6/107 |
| | | | | 250/492.1 |
| 2009/0272921 A1* | 11/2009 | Ballsieper | | G21F 1/12 |
| | | | | 250/515.1 |
| 2010/0176317 A1* | 7/2010 | Smith | | B32B 27/08 |
| | | | | 250/519.1 |
| 2011/0163248 A1* | 7/2011 | Beck | | G21F 3/02 |
| | | | | 250/516.1 |
| 2011/0165373 A1* | 7/2011 | Khandkar | | G21F 1/12 |
| | | | | 156/60 |
| 2013/0048887 A1* | 2/2013 | Yoder | | G21F 3/00 |
| | | | | 250/515.1 |
| 2015/0048209 A1* | 2/2015 | Hoyt | | B64G 1/58 |
| | | | | 264/308 |
| 2017/0032857 A1* | 2/2017 | Thomsen, III | | C23C 4/134 |

* cited by examiner

HIGH-PASS RADIATION SHIELD AND METHOD OF RADIATION PROTECTION

CROSS-REFERENCE TO RELATED APPLICATION

This application is a continuation-in-part of International Patent Application PCT/IB2019/057770, filed on Sep. 16, 2019, entitled "High-pass radiation shield and method of radiation protection", which is incorporated by reference herein in its entirety.

TECHNICAL FIELD

The disclosure relates generally to a radiation shield, and particularly, to an energy-selective attenuating of polychromatic radiation shield for reducing patient radiation dose and protecting in-plane (within radiation) radiosensitive and vulnerable organs during radiological examinations without degrading the image quality.

BACKGROUND ART

Radiological examinations use ionizing radiations to scan a patient's body. Ionizing radiations may harm patient safety and, more importantly, cause cancer.

According to the ALARA principle, the dose to patients should be reduced as low as reasonably achievable. Shielding different parts of the patient's body is an efficient method for dose reduction and protection of patient safety during radiological examinations such as computed tomography (CT), radiography, fluoroscopy, C-arm, angiography, etc. In the prior art, different shields have been designed and used for the protection of patients. These shields may be categorized into two different groups: 1) the shields that are used for protecting organs outside the Field of View (FOV) during radiological examinations. The FOV is the maximum diameter of the area of the scanned object that is exposed directly and is represented in the reconstructed image. Outside the FOV, the organs are not in direct exposure and are mostly exposed by scattered radiations. Hereafter, this type of shielding is named out-of-plane shielding. 2) The shields that are used for protecting some organs inside the FOV. Organs inside the FOV are the target area for imaging and are exposed directly by a great amount of radiation. Hereafter, this type of shielding is named in-plane shielding. It should be noted that these two types of shielding are completely different from each other. The out-of-plane shielding is intended to block all of the radiations with different energies and this type of shielding has no interference with the image quality. In contrast, the in-plane shielding is partially transparent to radiations and may affect the image quality and cause artifacts and should be used cautiously.

The out-of-plane shielding is accomplished by simply positioning a thick lead garment or lead-free garment over the organs. In this type of shielding, it is desired to attenuate and block all kinds of photons in all energy ranges. The in-plane shielding is used when a vulnerable and radiosensitive organ falls inside the radiation field. This method of shielding may efficiently reduce the patient dose and reduce the chance of cancer to radiosensitive organs; however, it may affect and degrade the image quality seriously and hence reduce the diagnostic accuracy.

In-plane shielding of organs is a challenging issue because it should reduce the radiation dose in a target area without corrupting the image quality. For reducing the degrading effects of the shield on image quality, the shield should be partially transparent to the radiation so that it be able to reduce radiosensitive organs dose while preserving the signal to noise ratio (SNR). Selecting appropriate materials as radiation absorbing material has a critical role in the successfulness of this method.

Most of the existing shields in the prior art are in the category of the out-of-plane shielding and few shields have been designed for the aim of in-plane shielding. Using thin layers of bismuth (Bi) shield for protecting radiosensitive organs within the radiation field during CT scan is the first in-plane shielding method that was initiated in 1997 by Hopper et al (U.S. Pat. No. 6,320,938 B1). It was claimed that using the Bi shielding, reduced the radiosensitive organs dose between 40% and 60% during CT examinations. After disclosing of this disclosure, several studies were conducted to evaluate the effects of the Bi shielding on image quality; they indicated that the in-plane Bi shielding had considerable degrading effects on image quality.

In spite of severe degrading effects of the in-plane Bi shielding, it has been used for about 20 years and also is currently used in many imaging centers during CT examinations in the world. In November 2017, the American Association of Physicists in Medicine (AAPM) released a statement recommending against the Bi shielding during CT examinations due to its degrading effects on the image.

Degrading effects of the in-plane Bi shielding during CT scan is a long-lasting problem that has not been solved in the prior art and no other efficient in-plane shielding has been presented up to now.

SUMMARY OF INVENTION

The present disclosure responds specifically to the long-felt needs heretofore unmet by the prior art, and especially to overcome the inherent inadequacies of in-plane Bi shielding during CT examinations.

In this disclosure, a new radiation shield, named high-pass radiation shield, for reducing X-ray dose of a patient during radiological examinations without degrading image quality is disclosed. The high-pass shield comprising at least two sublayers, wherein the first sublayer comprising a first radiation attenuation material having an atomic number from 21 to 30 and the second sublayer comprising a second radiation attenuation material which is different from the first radiation attenuation material. The materials with atomic number of 56 or greater may be used in the second sublayer. The first sublayer is configured to partially attenuate a primary radiation beam emanating from a radiation source and the second sublayer is configured to attenuate secondary radiations emanating from the first sublayer. The weight of the second radiation attenuation material is not greater than the weight of the first radiation attenuation material. The first sublayer is closer to the radiation source than the second sublayer.

The first sublayer is configured to block or highly attenuate a first range of energies of radiation and pass or slightly attenuate a second range of energies of radiation emanating from an X-ray tube. The first range of energies have lower energies and contribute mostly on the patient's dose rather than image quality; whereas the second range of energies have higher energies and may pass easily through the patient's body and have the main role in the SNR and image quality. The second sublayer is configured to block or attenuate a third range of energies of radiation, between about 1 and 10 keV, emanating from the first sublayer. The high-pass shield may be used along with different types of radiology scanners including CT scan, radiography, fluoroscopy, C-arm, and angiography for reducing the patient dose without degrading image quality.

A system is disclosed in this disclosure configured for placement on a patient's body during radiological examinations for reducing the patient dose without degrading image quality. The system comprising a high-pass radiation shield conformed of at least two radiation attenuation sublayers and a spacer conformed of a radiation transparent material. The shield is configured to partially attenuate a primary radiation beam emanating from a radiation source and the spacer is configured to offset the shield from the patient's body. The first sublayer of the shield comprising a first radiation attenuation material having an atomic number from 21 to 30 and the second sublayer of the shield comprising a second radiation attenuation material which is different from the first radiation attenuation material. The lead equivalence of the shield may be between about 0.022 mm Pb equivalent and 0.18 mm Pb equivalent.

Furthermore, a method for partially attenuation of a primary X-ray beam applied to a target area on a patient during radiological examinations is disclosed. The method may reduce X-ray dose of an organ/organs located within the target area without degrading image quality. The method comprising the steps of: a) Placing a radiation attenuation system on the patient's body over the target area, said system comprising a high-pass X-ray shield conformed of at least two radiation attenuation sublayers and a spacer conformed of an X-ray transparent material, wherein the first sublayer of the shield comprising a first radiation attenuation material having an atomic number from 21 to 30 and the second sublayer of the shield comprising a second radiation attenuation material which is different from the first radiation attenuation material. The total thickness of the shield may between about 0.022 and 0.18 mm Pb equivalent. b) Aligning the system to be in-line with the primary radiation beam covering the organ/organs within the radiation field and not extending around the entire periphery of the patient so that the primary radiation beam passes through the system before reaching the organ/organs.

Technical Problem

The use of radiological examination such as computed tomography (CT), radiography, fluoroscopy, and angiography as diagnostic imaging technologies have increased significantly over the last decades. Radiological examinations use ionizing radiation which is very hazardous for patient safety. Efficient and user-friendly dose reduction methods are required for the protection of patient's organs, especially the radiosensitive organs including eyes, thyroids, breasts, testes, and gonads, during radiological examinations. This is more critical in children because they are as much as ten times more susceptible to radiation damages than adults.

The in-plane Bi shielding reduces radiation dose to superficial radiosensitive organs effectively by absorbing low energy photons; however, it attenuates high energy photons along with the low energy photons and causes SNR loss which, in turn, leads to image quality corruption.

In spite of dose reduction benefits, several studies have indicated degrading effects of the Bi shielding on image quality such as increasing in image noise, causing artifacts and changing in CT numbers. The corrupting effects of in-plane Bi shielding on image quality have caused major concerns about the accuracy of the images and have made its usage challenging in clinical examinations.

In November 2017, the AAPM released a statement recommending against Bi shielding application during CT scan due to its degrading effects on image quality.

Thus, notwithstanding the known drawbacks and continual efforts to upgrade the in-plane Bi shielding efficiency, the art has not adequately responded to date with the introduction of new materials specifically adapted for use in this type of shielding method.

The in-plane Bi shielding has only been used in CT scan in the prior art and has not been used in the case of other radiological examinations such as radiography, fluoroscopy, C-arm, and angiography due to the degrading effects of the in-plane shielding on the radiograph image quality and corrupting the diagnostic accuracy.

Solution to Problem

Photons energy in X-ray tubes of diagnostic radiology spans between about 10 keV up to 150 keV. Low energy photons (i.e. photons below 30 keV) could not pass through the patient's body and hence contribute mostly on patient's dose rather than the signal to noise ratio (SNR). In contrast, high energy photons could easily pass through the patient's body and play an important role in the SNR value and image quality. The low energy photons, hereafter is named useless photons, have no utility in the scanning procedure whereas the high energy photons, hereafter is named useful photons, are highly required to form a diagnostic image from the patient's body.

To reduce the patient dose without considerable loss in SNR, the energy of photons should be modulated in a targeted way so that low energy photons (useless photons) be removed from the spectrum that would otherwise be absorbed by the patient while preserving high energy photons (useful photons). A high-pass shield using high-pass X-ray absorbing material may be used for this aim; however, the material used in the shield composition will have a critical role in the success of this method.

To find appropriate high-pass materials for the aim of this disclosure, we defined an index named "High Pass Efficiency (HPE)" to measure the high-pass-ability of periodic table materials. This index measures the ratio of the mass attenuation coefficient of a given material in high energies to low energies, as following:

$$HPE = \frac{\text{mean}\left(\frac{\mu}{\rho}\right)_L}{\text{mean}\left(\frac{\mu}{\rho}\right)_H}$$

Wherein, $$\left(\frac{\mu}{\rho}\right)$$

indicates me mass attenuation coefficient of a given material; H and L indicate the high and low frequencies, respectively.

The higher HPE value of a material indicates the higher transmission ability of it for the high energy photons and higher attenuation ability of it for the low energy photons. In other words, the higher HPE indicates the efficiency of material for removing useless photons from the radiation spectrum while preserving useful photons.

To calculate the HPE index, the mass attenuation coefficients of materials in energies between 10-120 keV, are extracted from NIST database and categorized in two high and low energy groups; then, the mean mass attenuation coefficient of a material in high energy photons is calculated and divided to the mean mass attenuation coefficients of it in low energies. The photons with the energy of equal or less than 30 keV were considered as the low energy photons and the photons with the energy of equal or more than 50 keV are considered as the high energy photons. Then, the HPE index was calculated for all of the periodic table materials. It was found that the material with the atomic number from 21 to 30 had the highest HPE (FIG. 6). So, for construction of the high-pass shield, the first radiation attenuation material is selected from the group of materials with the atomic number between 21 and 30 (named high-pass material) consisting of Sc, Ti, V, Cr, Mn, Fe, Ni, Cu, and Zn or combination thereof.

The HPE value of the high-pass materials is about 90 to 95. The Bi has been frequently used as an in-plane shielding material during CT scan in the past while it's HPE value is only 19; this means that it was not at all a suitable choice for this purpose. As an example, a single layer (0.06 mm lead equivalent attenuation) of both Bi and Zn (Z=26) attenuates 99.99% of 10 keV photons (useless photons) and there is no considerable difference between them in low energies; however, a single layer of the Bi attenuates 68% of 100 keV photons (useful photons) while a single layer of the Zn, as a high-pass material, attenuates only 18% of 100 keV photons.

Advantageous Effects of Invention

Shielding in accordance with the present disclosure exhibit materially improved characteristics when compared with the historic material of choice for such in-plane shielding.

The high-pass shields reduce the in-plane radiosensitive organs dose as the conventional in-plane Bi shielding whereas they do not have the degrading effects of the Bi shielding on image quality.

The high-pass shielding may provide about 20% higher dose reduction than the conventional Bi shielding at the equivalent image quality.

The high-pass shielding may provide between about 40% and 55% dose reduction in the case of radiosensitive organs during CT scan examinations while do not cause any artifact in the reconstructed images. Also, the high-pass shield may provide patient dose reduction by between about 30% and 50% during radiography, fluoroscopy, and angiography without degrading the image quality.

The high-pass radiation shield is flexible, cheap and user-friendly for shielding patient organs, especially the radiosensitive organs during radiological examinations. This shield may be used in all generation of the radiological scanners all around the world without special needs for operators training.

BRIEF DESCRIPTION OF DRAWINGS

Several embodiments of the present disclosure are presented in the following drawings.

DESCRIPTION OF EMBODIMENTS

Figure 1:
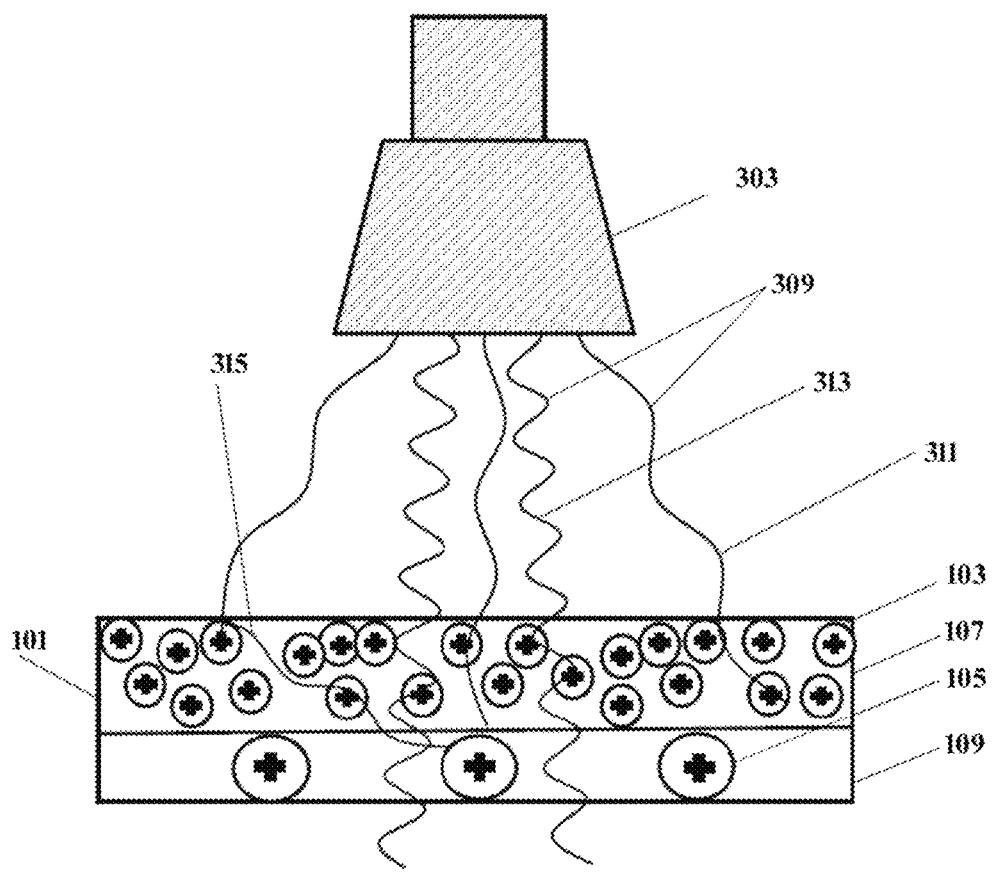
FIG. 1 indicates a high-pass radiation shield structure, composition, and the mechanism of radiation interaction with it, consistent with one or more exemplary embodiments of the present disclosure.

FIG. 1 shows a radiation shield 101, named high-pass radiation shield. The high-pass shield 101 may be useful in energy-selective blocking and/or attenuating of a polychromatic radiation 309 emanating from a radiation source 303, and assisting in the protection and dose reduction of a patient during radiological examinations such as CT, radiography, fluoroscopy, C-arm, and angiography without degrading image quality. The high-pass shield 101 may be used for attenuating of radiations 309 provided by an X-ray source 303 over a wide range of energies from the energy of 60 kVp up to 150 kVp. The shield 101 may selectively shroud or protect patient's organs placed within the radiation field of view (FOV) during radiological examinations.

A polychromatic radiation 309 produced by an X-ray tube 303 may have a first range of energies 311 or a first bandwidth of frequencies and a second range of energies 313 or a second bandwidth of frequencies, wherein the second range of energies are higher in energy than the first range of energies and the second bandwidth of frequencies are higher in frequency than the first bandwidth of frequencies.

The high-pass shield 101 may have two sublayers, wherein the first sublayer 107 is made of a first radiation attenuation material 103 and the second sublayer 109 is made of a second radiation attenuation material 105. The first radiation attenuation material 103 may be used to block or highly attenuate the first range of energies and pass or slightly attenuate the second range of energies in the polychromatic radiation spectrum 309 emanating from the X-ray tube 303. More specifically, the first radiation attenuation material 103 may be configured to block or highly attenuate low energy photons (useless photons) 311 and pass or slightly attenuate high energy photons (useful photons) 313 in the polychromatic radiation 309 spectrum.

Secondary radiations 315 may be produced after the interaction of primary radiations 309 with the first radiation attenuation material 103 that may have a third range of energies. The second radiation attenuation material 105 may be used to attenuate the secondary radiations 315 emanating from the first sublayer 107 having the third range of energies. The second range of energies are higher in energy than the first range of energies and the first range of energies are higher in energy than the third range of energies.

The first range of energies may be between about 10 keV and 30 keV and the third range of energies may be between about 1 keV and 10 keV; the radiations with the above-mentioned energies may not have enough energy to pass through the patient's body and are absorbed mostly by the patient and hence do not contribute in image quality and SNR. The third range of energies is very dangerous to patient safety due to having higher linear energy transfer (LET) rate. Highly attenuating or blocking the first and third range of energies and slightly attenuating or not attenuating the second range of energies through the high-pass shield may reduce the patient dose without considerable loss in SNR and image quality.

The degrading effects of the high-pass shield 101 on image quality is a function of some technical features including a) the material of the first sublayer 103, b) the material of the second sublayer 105, c) total thickness of the shield 101, d) thickness of the second sublayer 109 or second to first radiation attenuation materials weight ratio, and e) order of sublayers. To achieve a desired efficiency for the high-pass shield, these technical features should be selected correctly.

In the high-pass shield 101, the first sublayer 107 may be configured to be positioned closer to a radiation source 303 than the second sublayer 109.

The first radiation attenuation material 103 may be selected from the group of high-pass materials having an atomic number from 21 to 30 consisting of Sc, Ti, V, Cr, Mn, Fe, Co, Ni, Cu, and Zn or compound thereof, alone or in combination thereof. The material of the second sublayer 109 is different from the material of the first sublayer 107. The materials that produce few characteristic X-rays or their characteristic X-rays are not of sufficient energy to reach the patient's body may be used in the second sublayer. Without limitation, the second radiation attenuation material 105 may be selected from a group of materials with an atomic number of 56 or more. Non-limiting examples of such elements include Bi, tungsten (W), and lead (Pb). Using the second radiation attenuation material 105 may adversely affect image quality because they may absorb high energy photons along with low energy photons. The thickness of the second sublayer is an important feature that may be optimized to achieve a compromise between the secondary radiation exposure reduction and image quality. To do so, the weight of the second radiation attenuation material 105 should not be greater than the weight of the first radiation attenuation material 103. More preferably, the weight ratio of the second radiation attenuation material 105 to the first radiation attenuation material 103 may be about 1:8 or less for preserving image quality. The second sublayer 109 with 0.025 mm Pb equivalent or less may be used for highly attenuation of secondary radiations.

In some embodiments, particles of a radiation attenuation material may be held together with a polymer. In embodiments where the attenuating material includes a sufficient amount of the polymer, the particles of attenuating material may be dispersed throughout the polymer. As non-limiting examples, the Silicone polymers, viscoelastic vinyl polymers, copolymers, and urethanes may be used as an elastomeric medium. The weight ratio of the radiation attenuation materials to the polymeric matrix may be in the range of from about 1:3 to about 3:1.

Different thicknesses of the shield 101 may be constructed for using during the various type of radiological examinations. The thickness of the shield 101 may be determined by considering the amount of attenuation and image quality that is desired. To reduce a patient dose without degrading image quality, the thickness of the shield may be selected in a way to have a radiation attenuation factor of between about 25% and 82% of X-rays at 120 kVp. In another embodiment of the present disclosure, different shields that attenuate 25%, 43%, 66%, 72%, and 82% of X-rays at 120 kVp, half-value layer (HVL)=5.7 mm of Aluminum (Al) have been successfully constructed and used as the high-pass shields. Hereafter, we refer to thicknesses ½, 1, 2, 3, and 4 of the high-pass shield as representing 25%, 43%, 66%, 72%, and 82% attenuation at 120 kVp, HVL=5.7 mm Al. The thickness 1 of the high-pass shield has transmission attenuation properties in the kVp of 80 and 100 as follows: 80 kVp=55%, HVL=3.85 mm Al; 100 kVp=50%, HVL=4.87 mm Al. The thicknesses ½ and 1 of the high-pass shields may be used in radiology examinations and the thickness 2, 3, and 4 may be used in CT scan examinations for protection of patients. Using the shields thicker than the thickness 1 in radiology and thicker than the thickness 4 in computed tomography may adversely affect image quality. In some applications, such as calcium scoring by computed tomography, the shields with the thickness of 5 or 6 may be used.

The thickness of a shield may be expressed in term of: 1) physical dimension, 2) lead equivalence, or 3) equivalent radiation attenuation factor. The thickness 1 of the high-pass shield is equivalent to 0.045 mm Pb. Accordingly, the thickness ½, 2, 3, 4, 5, and 6 of the high-pass shields have Pb equivalence of 0.022, 0.09, 0.135, 0.18, 0.225, and 0.27 mm Pb equivalent, respectively. The high-pass shields with the thickness of about 0.27 mm Pb equivalent or less may be used during radiological examinations. More preferably, the thickness of the high-pass shield may be about 0.18 mm Pb equivalent or less. The thickness of the second sublayer may not be greater than 0.025 mm Pb equivalent. Different materials may be used in the first and second sublayer of the high-pass shield that may have different physical thickness for the same radiation attenuation factor. So, in this disclosure, the equivalent radiation attenuation factor or lead equivalence were more preferred to indicate the high-pass shield thicknesses rather than using the physical dimensions.

Figure 2:
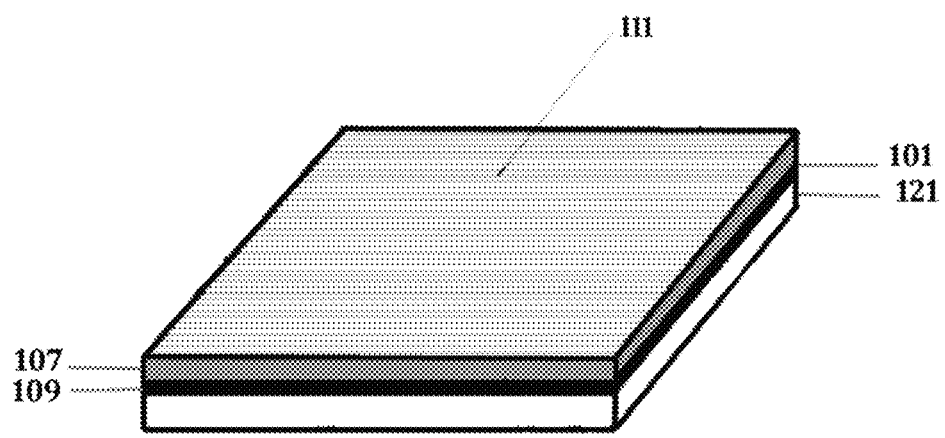
FIG. 2 shows a radiation attenuation system including a high-pass radiation shield and spacer that may be used during radiological examinations, consistent with one or more exemplary embodiments of the present disclosure.

This disclosure also includes a radiation attenuation system 111 configured for placement on a patient's body for reducing the patient dose during radiological examinations (FIG. 2). The system 111 comprising a spacer 121, which is positionable over the patient's body and a radiation shield 101 attached and secured to the spacer 121. The shield 101 may be a high-pass radiation shield comprising at least two radiation attenuation sublayers, wherein the first sublayer 107 comprising a first radiation attenuation material having an atomic number from 21 to 30 configured for partially attenuating of a primary radiation beam emanating from an X-ray tube and the second sublayer 109 comprising a second radiation attenuation material which is different from the first radiation attenuation material configured for attenuating of characteristic X-rays emanating from the first sublayer. The first radiation attenuation material is selected from the group of materials consisting of scandium, titanium, vanadium, chromium, manganese, iron, cobalt, nickel, copper, and zinc or compound thereof, alone or in combination. The material that produces few characteristic X-rays or its characteristic X-rays are not of sufficient energy to reach the patient's body may be preferred as the second radiation attenuation material. Without limitation, the materials such as bismuth or tungsten may be used in the second sublayer. The second radiation attenuation material may adversely affect image quality. To preserve image quality, the weight of the second radiation attenuation material should not exceed the weight of the first radiation attenuation material. The thickness of the second sublayer 109 may be about 0.025 mm Pb equivalent or less; furthermore, the second sublayer 109 is patient-adjacent layer and is configured to be positioned closer to the patient than the first sublayer. The Spacer 121 may be an X-ray transparent material with the thickness of 5 cm or less.

Figure 3:
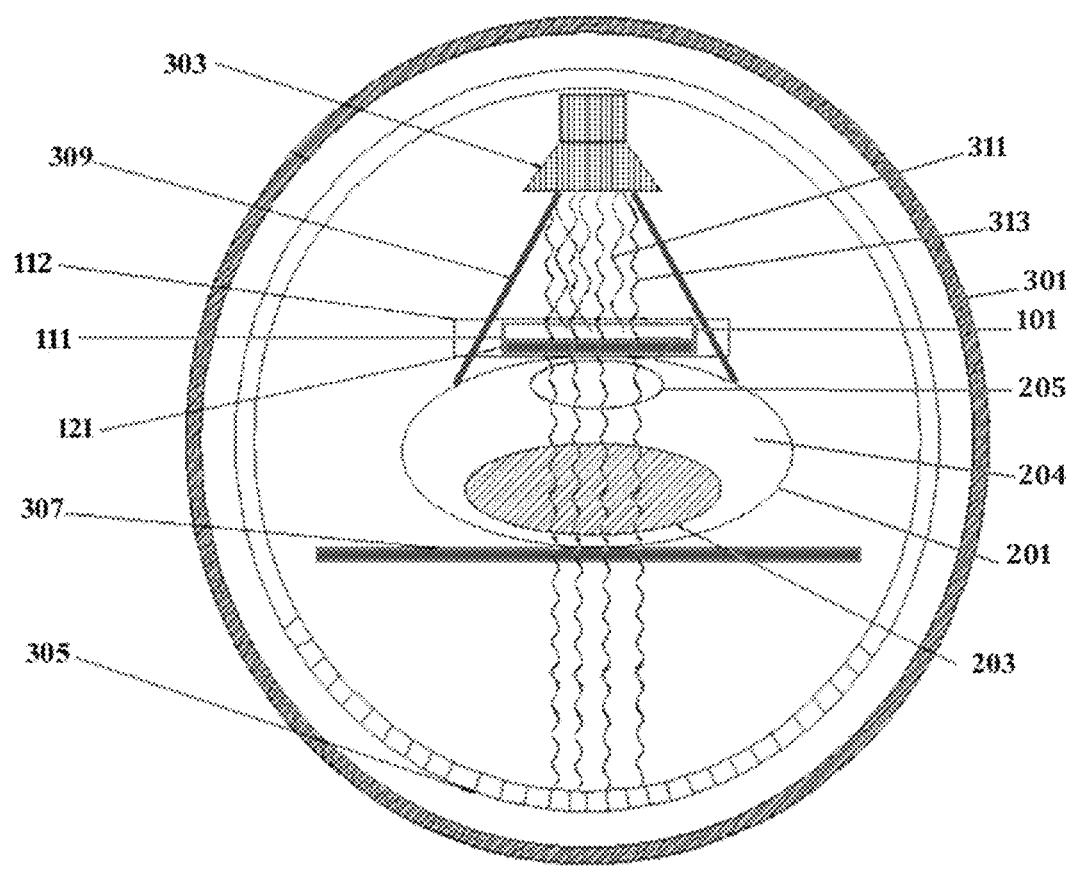
FIG. 3 shows—a method of using a radiation attenuation system during CT scan, consistent with one or more exemplary embodiments of the present disclosure.

The present disclosure is also directed to a method of use for said radiation attenuation system 111 during radiological examinations (FIG. 3). This method may be used for partially attenuating a primary X-ray radiation beam 309 applied to a target area 204 on a patient during radiological examinations to reduce the X-ray dose of an organ/organs 205 located within the target area 204 without degrading image quality. This method comprising the step of positioning the radiation attenuation system 111 on the patient's body 201 over the target area 204. Furthermore, in this method the radiation attenuation system 111 may be aligned to be in-line with the primary radiation beam 309 covering the organ 205 within the radiation field and not extending around the entire periphery of the patient's body 201 so that the primary radiation beam 309 passes through the system 111 before reaching the organ 205. When the primary radiation beam 309 passes through the system 111, low energy photons 311 are removed by the high-pass shield 101 whereas high energy photons 313 pass through it; as a result, the patient dose is reduced without degrading image quality. A cover 112 may be used for housing the system for easy use and maneuver; also, the cover 112 may be disposed of after single-use to prevent bacterial or viral transfer from patient to patient.

The radiation attenuation system 111 and its method of use may be applied for reducing the dose of radiosensitive organs such as eyes, thyroids, breasts, and gonads during computed tomography examinations. FIG. 3 indicates a CT scan 301 in accordance with the present disclosure. The CT scan 301 includes an X-ray tube 303 that emits polychromatic radiations 309. Detectors 305 are spaced from the tube in the path of radiation 309. The detectors 305 detect radiations striking them for generating a diagnostic image. A patient 201 is placed on a couch 307 between the X-ray tube 303 and detectors 305 so that the radiation 309 pass through a cross-section of the patient's body before striking to the detectors 305. Body cross-section or target area 204 includes a target organ 203 that is the subject of the CT scan and a radiosensitive organ 205 that is also within the X-ray beam. The system 111 is located inside the cover 112 and is placed on the patient's body 201 over the radiosensitive organ 205 so that the shield 101 is positioned closer to the X-ray tube 303 than the spacer 121 and the spacer 121 is located in a contact position with the patient's body 201. The shield 101 shrouds the entire radiosensitive organ 205 whereas it does not extend around the entire periphery of the patient's body 201. The CT scan is conducted according to conventional protocols and technical parameters. The tube 303 revolves around the patient 201 and when it passes from the anterior portion of the patient's body 201, the radiosensitive organ 205 is placed in direct exposure of the tube 303. In these views, the shield comes between the tube 303 and radiosensitive organ 205 and absorbs low energy photons 311 (useless photons) from the spectrum 309 that would otherwise be absorbed by the radiosensitive organ 205 and reduces its dose without degrading image quality.

The system 111 may include a shield with the thickness of between 2 and 6 (with the Pb equivalence of 0.09 mm Pb equivalent to 0.27 mm Pb equivalent). More preferably, the system 111 may include a shield with the thickness of between 2 and 4. The system 111 may provide between about 40% and 55% dose reduction in the case of radiosensitive organs 205 located within the radiation 309 field during CT examinations without degrading image quality. The system 111 may cause noise and CT number change less than about 15% and 5 HU, respectively, in a region of interest within the image at a distance of 3 cm from the shield 101. The shape of the shield 101 may be conformed to the shape of the patient's body 201 or patient's vulnerable organs 205.

The high-pass shield may be used along with the CT scanners equipped with the automatic exposure control (AEC) technology. For having the dose reduction benefits of both methods, the shield may be placed on the patient after taking the topogram; first, the radiograph (topogram) is taken, then the shield is placed on the patient's body. Placing the high-pass shield before the radiograph will lead to the tube current increase that will counter the dose reduction by the shield.

Figure 4:
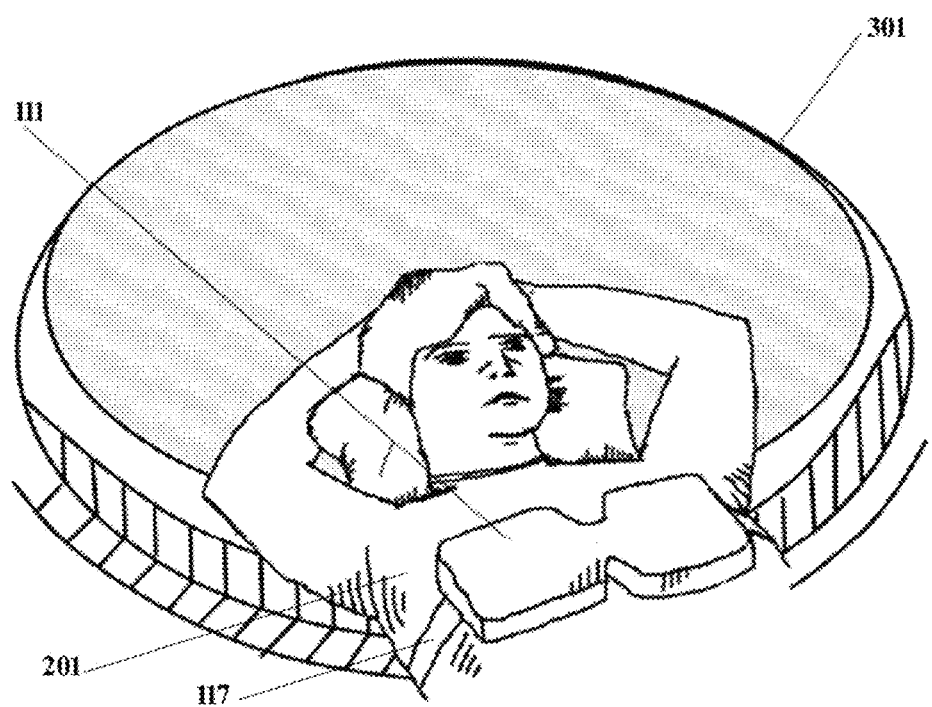
FIG. 4 shows a method of using a radiation attenuation system for protection of breasts during CT scan, consistent with one or more exemplary embodiments of the present disclosure.

FIG. 4 shows a patient undergoing thoracic CT 301 examination in accordance with the present disclosure. The breasts are radiosensitive organs that are located within the radiation field and are exposed to the X-ray beam as an incidental by-product of a thoracic CT scan. Before doing thoracic CT scan, the system 111 is enclosed inside a cover and the system is placed on the patient's body 201 over the radiosensitive organ. Two strips 117 exist in the sides of the cover that may be fastened to the patient's body 201 for preventing the possible displacements of the shield especially in the case of children. The shield is located within the image to be formed by the scanner. The CT scan is conducted according to conventional protocol and technical parameters. The shield protects the patient's breasts when the scanner 301 exposes directly toward the breasts and reduces the breasts surface dose by about 50% as compared to the same CT scan made without the shield. The diagnostic quality of the image is unaffected by the shield 101.

Figure 5:
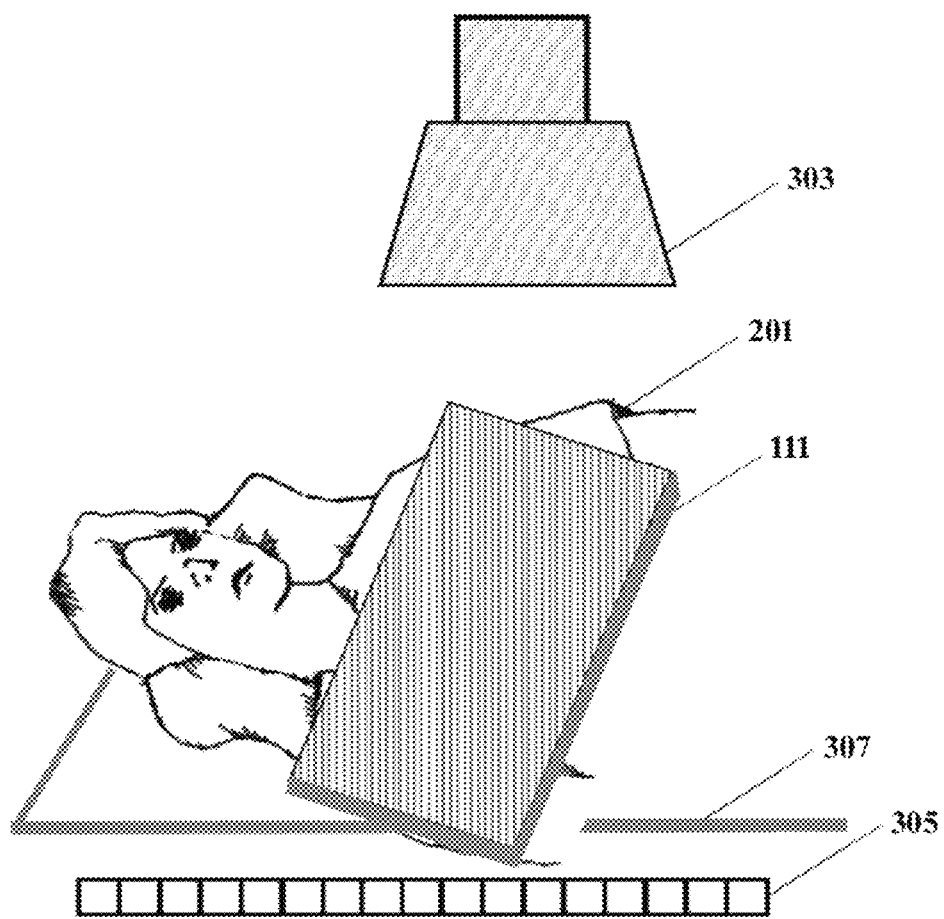
FIG. 5 indicates the method of using a radiation attenuation system for protection of a patient during radiography, consistent with one or more exemplary embodiments of the present disclosure.

The system and its method of use may be applied for reducing a patient dose during radiological examinations including radiography, fluoroscopy, C-arm, and angiography. The system may reduce the patient radiation dose during the radiological examinations without degrading image quality. The method is applicable in the case of all existing radiology scanners. FIG. 5 indicates a radiography in accordance with the present disclosure. The scanner includes an X-ray tube 303 that emits polychromatic radiations. Detectors 305 are spaced from the tube 303 in the path of radiation. The detectors 305 detect radiations striking them for generating a diagnostic image. A system 111 including a high-pass shield and a spacer is placed on the patient's body 201 over the entire FOV to cover all the target area. The spacer may be used to prevent low energy secondary radiations (less than 2 keV) from reaching the patient's body 201. This low energy photons may be produced by low Z materials such as silicon that may be used in the shield composition. The X-radiations are produced by source 303 and first interact with the high-pass shield by which low energy photons are mostly removed from the spectrum whereas high energy photons pass through the high-pass shield. Then, the passed photons through the shield interact with the patient 201 which is lied on the couch 307. Finally, the passed radiations through the system 111 and the patient's body 201 are gathered by detectors 305 to make a diagnostic image from the patient's body 201. The thickness of the high-pass shields used for protection of patient may be selected considering the X-ray tube kVp. This means that the amount of the patient's dose reduction using the high-pass shield depends on the tube kVp used during radiography. The higher the kVp, the higher the patient's dose reduction. As a non-limiting example, a thickness 1 of the high-pass shield may be used when the kVp of the tube is 100 which leads to a dose reduction by about 50%; whereas, a thickness ½ of the high-pass shield may be used when the kVp of the tube is 80 which leads to a dose reduction by about 36%. Other thicknesses of the high-pass shield may be used to reduce the patient dose without degrading image quality. The high-pass shield may reduce the patient dose by between about 30% and 50% during radiological examinations without degrading image quality depending on the tube kVp.

Without limitation, the high-pass shield may be constructed in the other forms such as garment, apron, filter, foil, sheet, etc. or may be attached to other articles such as garment or cloth; also, the high-pass shield may be attached to the frontal part of the X-ray tube as a filter.

EXAMPLES

Example 1: Evaluation of the HPE Index for the Periodic Table Materials

Figure 6:
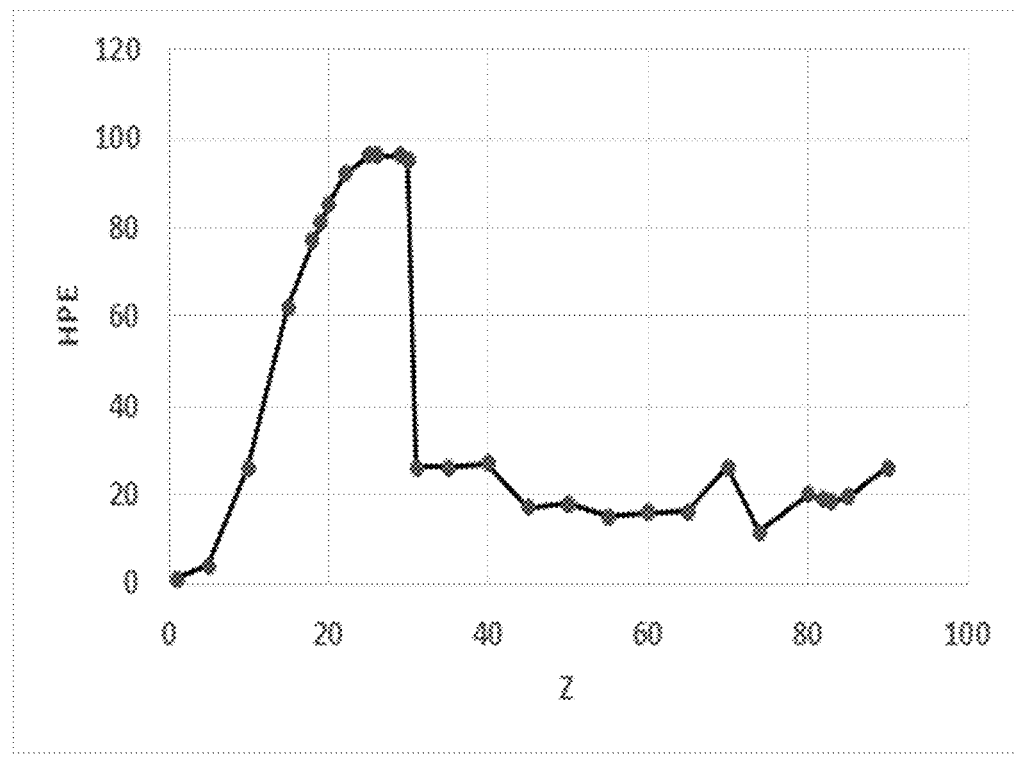
FIG. 6 indicates the HPE index for periodic table materials, consistent with one or more exemplary embodiments of the present disclosure.

In this disclosure, the HPE value was defined to identify the best available high-pass materials to construct the high-pass shield. To do so, the HPE value was calculated for periodic table materials with atomic numbers from 1 to 90; photons with energies of 10, 20, and 30 keV were considered as the low energy photons and photons with energies of 60, 80, and 100 were considered as the high energy photons. As can be seen from FIG. 6, materials with atomic numbers from 21 to 30 have the highest HPE values and hence, these materials are considered as the high-pass materials. As a result, the first radiation attenuation material in the high-pass shield construction is selected from this group of materials consisting of Sc, Ti, V, Cr, Mn, Fe, Ni, Co, Cu, and Zn or compound thereof. Of those, the Fe, Ni, Cu, and Zn are preferred due to having higher densities and higher HPE value. The HPE values of the high-pass materials are about 95. This means that their mass attenuation coefficients for the useful photons are 95 times less than their mass attenuation coefficient for the useless photons.

Example 2: Evaluation of the Attenuation Values of Different High-Pass Shields For comparing the effects of high-pass shields on image quality with those of the conventional Bi shield during radiological examinations, it is required to construct all the shields with the same attenuation values. To do so, different thickness 1 of high-pass shields as well as a thickness 1 of Bi shield were designed and constructed and their attenuation values were measured. The high pass shields were constructed using the high-pass materials of Fe, Ni, Cu, and Zn as the first radiation attenuation material and the Bi as the second radiation attenuation material with the weight ratio of 9:1. Silicon rubber is used as the polymeric matrix. An X-ray tube was used for producing a uniform field of x-ray at 120 kVp, HVL=5.7 mm Al. A high sensitivity semiconductor detector (NOMEX multimeter, PTW-Freiburg, Germany) was placed in front of the tube with 100 cm distance from the source. The shields were placed between the source and dosimeter with 80 cm distance from the x-ray tube. A known intensity of radiation was exposed and the attenuation values of different shields were measured (Table 1). The measurements were repeated for 5 times for obtaining a reliable average.

TABLE 1

Attenuation values of thickness 1 of high-pass shields and Bi shield at 120 kVp, HVL = 5.7 mm Al

| Shield composition | Dose (mGy) | Dose Reduction (%) |
|---|---|---|
| No shielding | 2.9 | — |
| Fe—Bi | 1.65 | 43.1 |
| Ni—Bi | 1.63 | 43.7 |
| Cu—Bi | 1.63 | 43.7 |
| Zn—Bi | 1.67 | 42.4 |
| Bi | 1.66 | 42.7 |

Example 3: Evaluation of the Dose Reduction in Eye, Thyroid, Gonad, and Breast Tissue by the High-Pass Shielding During CT Scans Prototype thickness 3 of the high-pass breast, eye, thyroid, and gonad shields, as well as a thickness 3 of Bi shield, were used in this study. The high-pass shields were constructed using the Zn as the first radiation attenuation material and the Bi as the second radiation attenuation material, with the weight ratio of 9:1, and the RTV silicon as the polymeric matrix. An Alderson Rando female anthropomorphic phantom was placed at the CT scanner couch. The phantom was scanned using a 16 slice CT scanner (Philips, Brilliance) with the routinely used protocols and parameters. The automatic exposure control (AEC) was set on during imaging. Thermoluminescence dosimeters (TLD) were used for skin entrance dose (ESD) measurement. For each measurement in the case of breast, eye, thyroid, and gonad organs, three fresh and calibrated TLDs (TLD-100 3×3×0.9-mm chips, Harshaw) were placed on the left and right organs. Scans were repeated 5 times for each organ, to reduce the statistical error of the TLD readings. The mean dose of the 6 TLDs was considered as each organs dose. For measuring the dose reduction by the high-pass shielding (Zn—Bi), first a scanogram (scout view) was obtained and the craniocaudal scanning range was planned. The shield was not placed over the organs in this step because positioning the shield in this step will disrupt the dose reduction by AEC method. After taking the scout view of the target area, the shield and a 3 cm spacer altogether were put inside a cover; then the cover containing both shield and spacer was placed over the radiosensitive organ. The CT scan was performed with conventional protocols. The dosimetry results are indicated in table 2. The results indicate that using the thickness 3 of high-pass shielding as well as the Bi shielding decreases the entrance surface dose of the radiosensitive organs between about 40-55%.

TABLE 2

Mean entrance skin dose of breast, thyroid, eye, and gonads during thoracic, neck, head, and pelvic and stomach CT scans, respectively, with and without the high-pass and Bi shields with the thickness 3

|  | 1T Shields | ESD (mGy) | Dose Reduction (%) |
| --- | --- | --- | --- |
|  | Breast - No shield | 22.63 ± 0.92 | — |
| Thickness 3 | high-pass shield (Zn—Bi) | 10.79 ± 1.1 | 52.3 |
| Breast Shield | Bi shield | 10.67 ± 0.82 | 52.8 |
|  | Thyroid - No shield | 21.1 ± 0.77 | — |
| Thickness 3 | high-pass shield (Zn—Bi) | 10.51 ± 0.71 | 50.1 |
| Thyroid Shield | Bi shield | 10.34 ± 0.87 | 50.9 |
|  | Eye - No shield | 18.91 ± 1.08 | — |
| Thickness 3 | high-pass shield (Zn—Bi) | 10.85 ± 0.64 | 42.6 |
| Eye Shield | Bi shield | 11.12 ± 0.63 | 41.1 |
|  | Gonad - No shield | 24.1 ± 0.88 | — |
| Thickness 3 | high-pass shield (Zn—Bi) | 11.67 ± 0.75 | 51.6 |
| Gonad Shield | Bi shield | 11.62 ± 0.91 | 51.7 |

Figure 7:
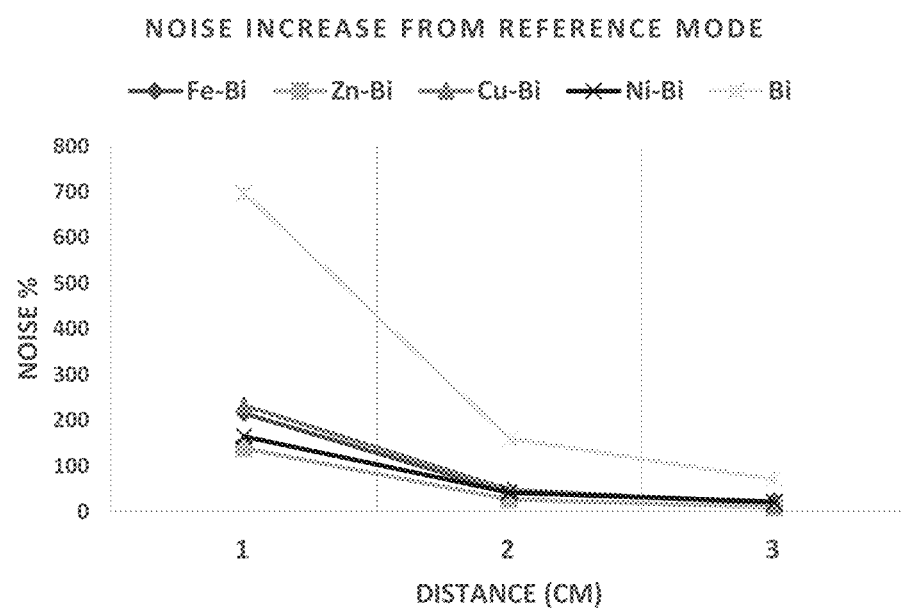
FIG. 7 and FIG. 8 indicate and compare the effects of a thickness 3 of high-pass gonad shields and a thickness 3 of a Bi gonad shield on CT numbers shift and image noise, consistent with one or more exemplary embodiments of the present disclosure.
Figure 8:
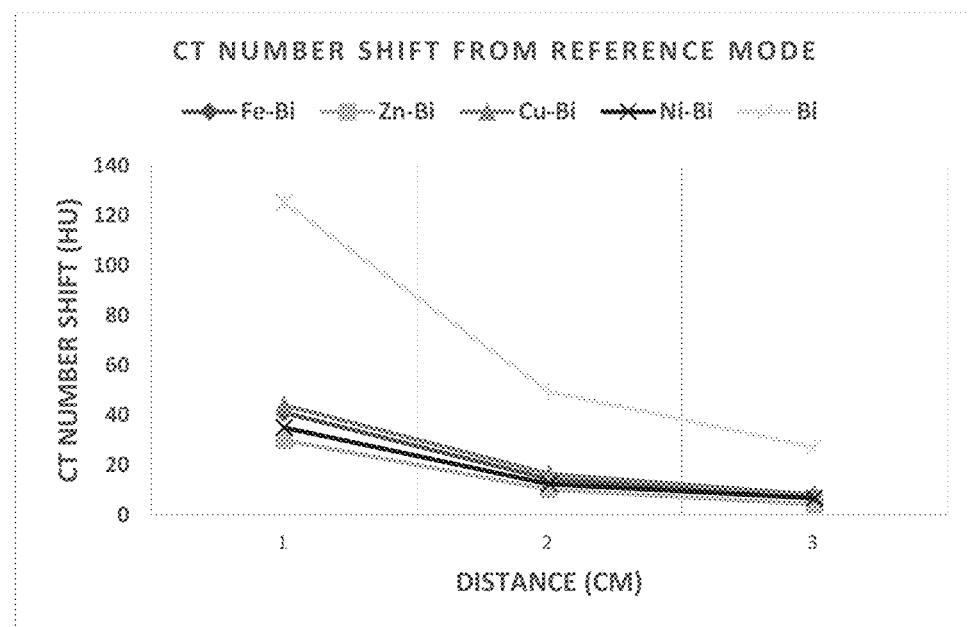

Example 4: Effects of the High-Pass Gonad Shielding on Image Quality During CT Scan: Uniform Phantom Study As another embodiment of this disclosure, four high-pass gonad shields (thickness 3) were constructed with the composition of Fe—Bi, Ni—Bi, Cu—Bi, and Zn—Bi. Image quality was quantitatively evaluated in a uniform CTDI head phantom by measuring and comparing the image noise and CT number shift in different regions of interests (ROI) before and after shielding procedure. In the uniform phantom, three 1 $cm^2$ ROIs were considered in the center of the phantom in different distances (1, 2, 3 cm) from the shield. Image noise was measured using the standard deviation of attenuation values (in Hounsfield units) in all ROIs. The CT numbers shift was measured using the difference between the Hounsfield units of an ROI before and after shielding procedure. The images of 10 successive slices were used for measuring the noise and CT number values for averaging and obtaining reliable data. The image qualities were compared with those of the thickness 3 gonad Bi shield. As can be seen from the FIGS. 7 and 8, the degrading effects of the high-pass shields on image quality are several times less than those of the conventional Bi shield. The results of this experiment were in accordance with the theoretical findings. Among the high-pass shields, the Zn—Bi shield had the best efficiency.

Figure 9:
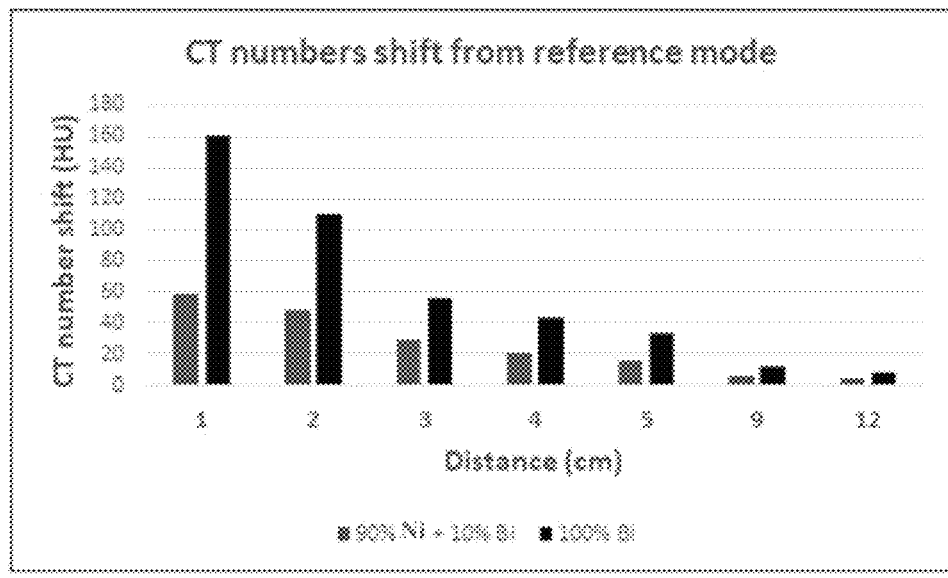
FIGS. 9-10 indicate and compare the effects of a thickness 3 of a high-pass eye shield and a thickness 3 of a Bi eye shield on CT numbers shift and image noise, consistent with one or more exemplary embodiments of the present disclosure.
Figure 10:
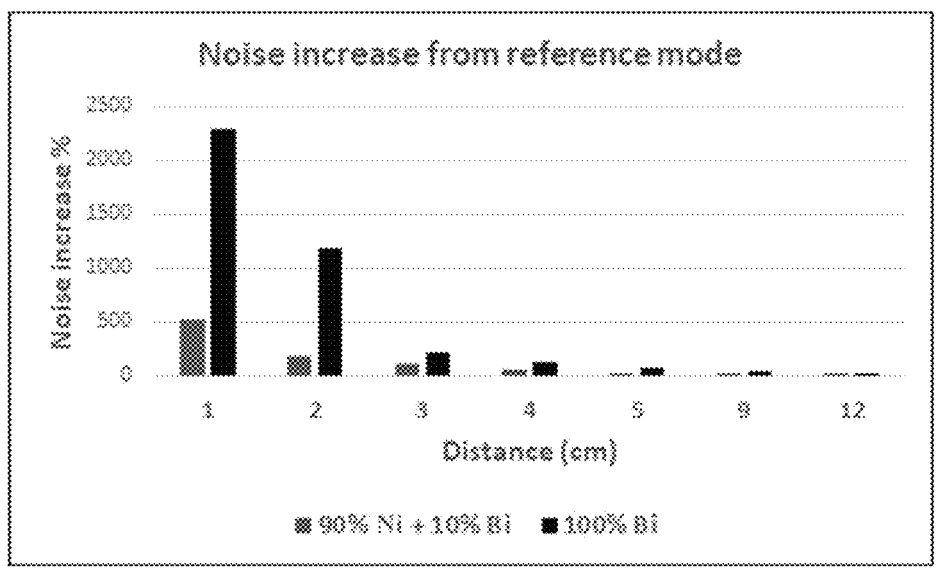

Example 5: Effects of the High-Pass Eye Shielding on Image Quality During CT Scan: Uniform Phantom Study The thickness 3 of high-pass eye shields, with the composition of the 90% Ni and 10% Bi were used in this study. Image quality was quantitatively evaluated in a uniform CTDI head phantom by measuring and comparing the image noise and CT number shift in different regions of interests (ROI) before and after shielding procedure. In the uniform phantom, seven 2 $cm^2$ ROIs were considered in the center of the phantom in different distances (0, 1, 2, 3, 4, 5, 9, 12 cm) from the shield. The images of 10 successive slices were used for measuring the noise and CT number value for averaging and obtaining reliable data. Using the high-pass eye shield caused a great reduction in the image noise and CT number shift in comparison to those of the Bi eye shield. The thickness 3 of high-pass shield reduced the image noise and CT number shift by 108% and 27 HU (at a distance of 3 cm from the shield) in comparison with the thickness 3 of Bi shield, respectively (FIGS. 9-10). This improvements in image quality acquired while the dose reduction of both shields was approximately identical.

The results of this experiment indicated that the degrading effects of the high-pass shielding on image quality are several times less than those of the conventional Bi shielding. Also, it was observed that the thickness 3 of the high-pass shield had the same image quality as the thickness 1 of Bi shield; in the other words, that high-pass shield had 20% more dose reduction than the Bi shielding.

Example 6: Effects of High-Pass Shielding on Image Quality During Computed Tomography and Radiography Examinations: Clinical Trial 200 patients were recruited and divided in 10 different groups (5 case and 5 control groups) having 20 patients in each group. Four CT shields including eye, thyroid, breast, and gonad shields with the thickness 3 and one radiography shield with the thickness ½ were used to cover target area in the intervention groups during examinations. A spacer of 3 cm width was used between the shield and patient. In control groups, patients underwent routine CT imaging without any further action. A questionnaire was filled by two radiologists about the image quality and different levels of artifacts were scored. In all groups, there was no significant difference between the intervention and control groups. Both radiologists declared that all the images are of normal diagnostic quality.

INDUSTRIAL APPLICABILITY

The radiosensitive organs such as eyes, thyroids, breasts, gonads, testes are very susceptible to radiation damages than other organs. During CT scan from different parts of the body such as head, neck, thorax, abdomen, and pelvis the radiosensitive organs may lie inside the FOV and are exposed to direct radiation. The high-pass shield may be simply positioned over the radiosensitive organs and reduces their dose significantly. A dose reduction of 40-55% is achievable using a thickness 3 of the high-pass shield without degrading image quality.

The high-pass shield may be used in different generations of CT scan including conventional, spiral, and multi-slice scanners. This shield also may be used in various modes of CT scan including ordinary CT, CT fluoroscopy, CT angiography and also the fusion imaging such as PET-CT and SPECT-CT.

The high-pass shield may be used for dose reduction during radiological examinations including radiography, fluoroscopy, C-arm, and angiography. A dose reduction by between about 30% and 50% is achievable using a thickness ½ and 1 of the high-pass shield without degrading image quality.

The high-pass shield may be used for modulating different type of radiations including X-ray, Gamma, alpha, and beta radiations.

What is claimed is:

1. An X-ray radiation shield to partially attenuate a primary X-ray radiation beam emission,
   the X-ray radiation shield comprising:
   a first sublayer comprising a first radiation attenuation material of atomic number from 21 to 30, wherein the first sublayer configured to block or highly attenuate a plurality of low-energy photons and pass or less attenuate a plurality of high-energy photons; and
   a second sublayer comprising a second radiation attenuation material of atomic number of 56 or more, wherein the second sublayer configured to attenuate a secondary radiation beam emanating from the first sublayer, wherein:
   a. a lead equivalence of the shield is in a range of 0.022 mm Pb equivalent to 0.18 mm Pb equivalent;
   b. a weight of the second radiation attenuation material is less than a weight of the first radiation attenuation material; and
   c. the second sublayer is positioned to patient-adjacent layer and the first sublayer is positioned on a top of the second sublayer.

2. The shield of claim 1, wherein the first radiation attenuation material is selected from the group of materials consisting of scandium, titanium, vanadium, chromium, manganese, iron, cobalt, nickel, copper, zinc, or a combination of at least two thereof.

3. The shield of claim 1, wherein the shield has a radiation transmission attenuation factor about 25% to 82% of a primary X-ray at 120 kVp.

4. The shield of claim 1, wherein the lead equivalent of the shield is not greater than 0.18 mm Pb equivalent.

5. The shield of claim 1, wherein a lead equivalence of the second sublayer is not greater than 0.025 mm Pb equivalent.

6. The shield of claim 1, wherein the radiation attenuation material is dispersed in a polymeric matrix.

7. An attenuating X-ray beam system to reduce a patient X-ray dose, the system comprising:
   a. a high-pass X-ray radiation shield positionable on a top of the patient's body over a target area configured to partially attenuate a primary radiation beam, wherein an attenuated X-ray beam reaches to the target area, the high-pass X-ray radiation shield comprising at least two radiation attenuation sublayers, wherein a first sublayer comprising a first radiation attenuation material including an atomic number from 21 to 30 and a second sublayer comprising a second radiation attenuation material, wherein the second radiation attenuation material has a different type of material from the first radiation attenuation material; and
   b. a spacer positionable between the shield and the patient's body, the spacer configured to offset the shield from the patient's body,
   wherein:
   a lead equivalence of the shield is in a range of 0.022 mm Pb equivalent to 0.18 mm Pb equivalent;
   a weight of the second radiation attenuation material is less than a weight of the first radiation attenuation material;
   the second sublayer is positioned to a patient-adjacent layer and the second sublayer is closer to the top of the patient's body than the first sublayer; and
   the spacer is made up of an X-ray transparent material.

8. The system of claim 7, wherein the first radiation attenuation material comprises scandium, titanium, vanadium, chromium, manganese, iron, cobalt, nickel, copper, zinc, or a combination of at least two thereof.

9. The system of claim 7, wherein the second radiation attenuation material comprises bismuth, tungsten, or a combination thereof.

10. The system of claim 7, wherein a thickness of the second sublayer is not greater than 0.025 mm Pb equivalent.

11. The system of claim 7, wherein the shield has a radiation transmission attenuation factor is less than 82% of a primary X-ray at 120 kVp.

12. The system of claim 7, wherein the system attenuates the X-ray beam in a range of 25% to 82% of a primary X-ray at 120 kVp.

13. The system of claim 7, wherein the system is configured to place on the patient's body over a radiosensitive organ during computed tomography examinations to reduce the X-ray dose of the radiosensitive organ, wherein the system has a radiation transmission attenuation factor in a range of 66% to 82% of a primary X-ray at 120 kVp and the X-ray dose of the radiosensitive organ is reduced about 40% to 55% without degrading an image quality.

14. The system of claim 7, wherein the system is configured to place on the patient's body over the target area during a radiography examination, a fluoroscopy examination, or an angiography examination to reduce the X-ray dose of the patient wherein the system has a radiation transmission attenuation factor in a range of 25% to 44% of the primary X-ray at 120 kVp and the X-ray dose of the patient is reduced about 25% to 50% without degrading an image quality.

15. An energy-selective radiation shield to attenuate a first range of energies and pass a second range of energies of a primary radiation beam, the energy-selective radiation shield comprising at least two sublayers, wherein:
   a first sublayer comprising a first radiation attenuation material, the first sublayer configured to block or highly attenuate the first range of energies and pass or less attenuate the second range of energies; and
   a second sublayer comprising a second radiation attenuation material, the second sublayer configured to attenuate a secondary radiation beam emanating from the first sublayer,
   wherein:
   a) the first radiation attenuation material comprises a group of radiation attenuation materials having a high-pass-efficiency (HPE) value of equal or greater than 50, the $$HPE = \frac{\left(\frac{\mu}{\rho}\right)_1}{\left(\frac{\mu}{\rho}\right)_2}$$

wherein the $$\left(\frac{\mu}{\rho}\right)_1$$

indicates a mean mass attenuation coefficient of the first radiation attenuation material at the first range of energies and the $$\left(\frac{\mu}{\rho}\right)_2$$

indicates a mean mass attenuation coefficient of the first radiation attenuation material at the second range of energies;
   b) the second radiation attenuation material comprises a group of radiation attenuation materials having a different atomic number from the first sublayer;
   c) a weight of the second radiation attenuation material is less than a weight of the first radiation attenuation material; and
   d) The first sublayer is positioned closer to a radiation source than the second sublayer.

16. The shield of claim 15, wherein the second range of energies comprise a higher energies than the first range of energies.

17. The shield of claim 15, wherein the first radiation attenuation material—comprises scandium, titanium, vanadium, chromium, manganese, iron, cobalt, nickel, copper, zinc, or a combination of at least two thereof.

18. The shield of claim 15, wherein the shield has a lead equivalence of about 0.27 mm Pb equivalent or less and the second sublayer of the shield has a lead equivalence of equal or less than 0.025 mm Pb equivalent.

19. The shield of claim 15, wherein a radiation transmission attenuation factor of the shield is equal or less than 82% of a primary radiation at 120 kVp.

20. The shield of claim 15, wherein the first radiation attenuation material comprises a group of materials having the HPE value of 70 or more.

* * * * *